US006278893B1

(12) United States Patent
Ardenkjær-Larson et al.

(10) Patent No.: US 6,278,893 B1
(45) Date of Patent: Aug. 21, 2001

(54) METHOD OF MAGNETIC RESONANCE IMAGING OF A SAMPLE WITH EX VIVO POLARIZATION OF AN MR IMAGING AGENT

(75) Inventors: Jan Henrik Ardenkjær-Larson; Oskar Axelsson; Klaes Golman; Georg Hansson; Ib Leunbach; Stefan Petersson; Lars-Göran Wistrand, all of Malmö (SE)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/169,148

(22) Filed: Oct. 9, 1998

Related U.S. Application Data

(60) Provisional application No. 60/076,924, filed on Mar. 5, 1998.

(30) Foreign Application Priority Data

Jan. 5, 1998 (GB) .................................................. 9800158
Jun. 25, 1998 (GB) .................................................. 9813795

(51) Int. Cl.[7] .................................................... A61B 5/055

(52) U.S. Cl. .......................... 600/420; 324/307; 324/309; 424/9.3

(58) Field of Search .................................... 600/410, 420; 324/307, 309; 424/9.3

(56) References Cited

U.S. PATENT DOCUMENTS 5,617,859 4/1997 Souza et al. .
6,125,654 10/2000 Honig .................................... 62/637

FOREIGN PATENT DOCUMENTS

WO 9737239 10/1997 (WO) .
WO 9801766 1/1998 (WO) .
WO 9830918 7/1998 (WO) .

OTHER PUBLICATIONS

XP–002098873, First Observation Of A Dynamic Polarization Of Monolayers of $He^3$ Adsorbed On Fluorocarbon Microspheres, Chapellier M et al. Proceedings of the $17^{th}$ International Conference on Low Temperature Physics, Lt–17, Karlsruhe, West Germany, Aug. 15–22, 1984, pp. 747–748 vol. 2.

XP–002098874, A Proposed Method for Polarizing Liquid $^3He$, Langer et al., Journal of Low Temperature Physics, Nov. 1984, USA, vol. 57, No. 3–4, pp. 249–263.

XP002098966, Optically Polarized $^{129}Xe$ in NMR Spectroscopy, Pietrass et al., Advanced Materials, Oct. 1995, VCH Verlagsgesellschaft, Germany, vol. 7, No. 10, pp. 826–838.

*Primary Examiner*—Ruth S. Smith
(74) *Attorney, Agent, or Firm*—Bacon & Thomas

(57) ABSTRACT

The present invention provides a method of magnetic resonance investigation of a sample, preferably of a human or non-human animal body, said method comprising the step of ex vivo polarisation of a high $T_1$ agent and wherein the polarising agent is optionally seperated from the high $T_1$ agent before the high $T_1$ agent is administered to the sample.

31 Claims, 3 Drawing Sheets

6
5
4
2
1
3

METHOD OF MAGNETIC RESONANCE IMAGING OF A SAMPLE WITH EX VIVO POLARIZATION OF AN MR IMAGING AGENT

CROSS-REFERENCE TO RELATED APPLICATION

This application claims the benefit of U.S. Provisional Application Ser. No. 60/076,924, filed Mar. 5, 1998.

FIELD OF THE INVNENTION

This invention relates to a method of magnetic resonance imaging (MRI).

BACKGROUND OF THE INVNENTION

Magnetic resonance imaging (MRI) is a diagnostic technique that has become particularly attractive to physicians as it is non-invasive and does not involve exposing the patient under study to potentially harmful radiation such as X-rays.

In order to achieve effective contrast between MR images of the different tissue types in a subject, it has long been known to administer to the subject MR contrast agents (e.g. paramagnetic metal species) which effect relaxation times of the MR imaging nuclei in the zones in which they are administered or at which they aggregate. Contrast enhancement has also been achieved by utilising the "Overhauser effect" in which an esr transition in an administered paramagnetic species (hereinafter an OMRI contrast agent) is coupled to the nuclear spin system of the imaging nuclei. The Overhauser effect (also known as dynamic nuclear polarisation) can significantly increase the population difference between excited and ground nuclear spin states of selected nuclei and thereby amplify the MR signal intensity by a factor of a hundred or more allowing OMRI images to be generated rapidly and with relatively low primary magnetic fields. Most of the OMRI contrast agents disclosed to date are radicals which are used to effect polarisation of imaging nuclei in vivo.

Techniques are now being developed which involve ex vivo polarisation of agents containing MR imaging nuclei, prior to administration and MR signal measurement. Such techniques may involve the use of polarising agents, for example conventional OMRI contrast agents or hyperpolarised gases to achieve ex vivo polarisation of administerable MR imaging nuclei. By polarising agent is meant any agent suitable for performing ex vivo polarisation of an MR imaging agent.

The ex vivo method has inter alia the advantage that it is possible to avoid administering the whole of, or substantially the whole of, the polarising agent to the sample under investigation, whilst still achieving the desired polarisation. Thus the method is less constrained by physiological factors such as the constraints imposed by the administrability, biodegradability and toxicity of OMRI contrast agents in in vivo techniques.

SUMMARY OF THE INVENTION

It has now been found that ex vivo methods of magnetic resonance imaging may be improved by using polarised MR imaging agents comprising nuclei capable of emitting magnetic resonance signals in a uniform magnetic field (eg MR imaging nuclei such as $^{13}C$ or $^{19}F$ nuclei) and capable of exhibiting a long $T_1$ relaxation time, preferably additionally a long $T_2$ relaxation time. Such agents will be referred to hereinafter as "high $T_1$ agents". Typically the molecules of a high $T_1$ agent will contain MR imaging nuclei in an amount greater than the natural abundance of said nuclei in said molecules (i.e. the agent will be enriched with said nuclei).

Thus viewed from one aspect the present invention provides a method of magnetic resonance investigation of a sample, preferably of a human or non-human animal body (eg. a mammalian, reptilian or avian body), said method comprising:

(i) subjecting a high $T_1$ agent to ex vivo polarisation;

(ii) optionally exposing the high $T_1$ agent to a uniform magnetic field (e.g. the primary field $B_o$ of the imaging apparatus of a weaker field e.g. 1 G or more);

(iii) where step (i) is carried out by means of a polarising agent, optionally separating the whole, substantially the whole, or a porion of said polarising agent from said high $T_1$ agent;

(iv) administering said high $T_1$ agent to said sample;

(v) exposing said sample to a second radiation of a frequency selected to excite nuclear spin transitions in selected nuclei eg the MR imaging nuclei of the high $T_1$ agent;

(vi) detecting magnetic resonance signals from said sample; and (vii) optionally, generating on image, dynamic flow data, diffusion data, perfusion data, physiological data (eg. pH, $pO_2$, $pCO_2$, temperature or ionic concentrations) or metabolic data from said detected signals.

Thus the invention involves the sequential steps of ex vivo polarisation of a high $T_1$ agent comprising nuclei capable of exhibiting a long $T_1$ relaxation time, administration of the polarised high $T_1$ agent (preferably in the absence of a portion of, more preferably substantially the whole of, any polarising agent), and conventional in vivo MR signal generation and measurement. The MR signals obtained in this way may be conveniently converted by conventional manipulations into 2-, 3- or 4-dimensional data including flow, diffusion, physiological or metabolic data.

Viewed from a further aspect the present invention provides a composition comprising a polarised $^{13}C$ or $^{19}F$ enriched compound together with one or more physiologically acceptable cariers or excipients.

Viewed from a further aspect the present invention provides a contrast medium comprising a polarised high $T^1$ agent being enriched with $^{13}C$ nuclei having a $T_1$ relaxation time of 2 s or more in solution at magnetic fields of 0.005–10 T, together with one or more physiologically acceptable carriers or excipients.

DETAILED DESCRIPTION OF THE INVENTION

Figure 1:
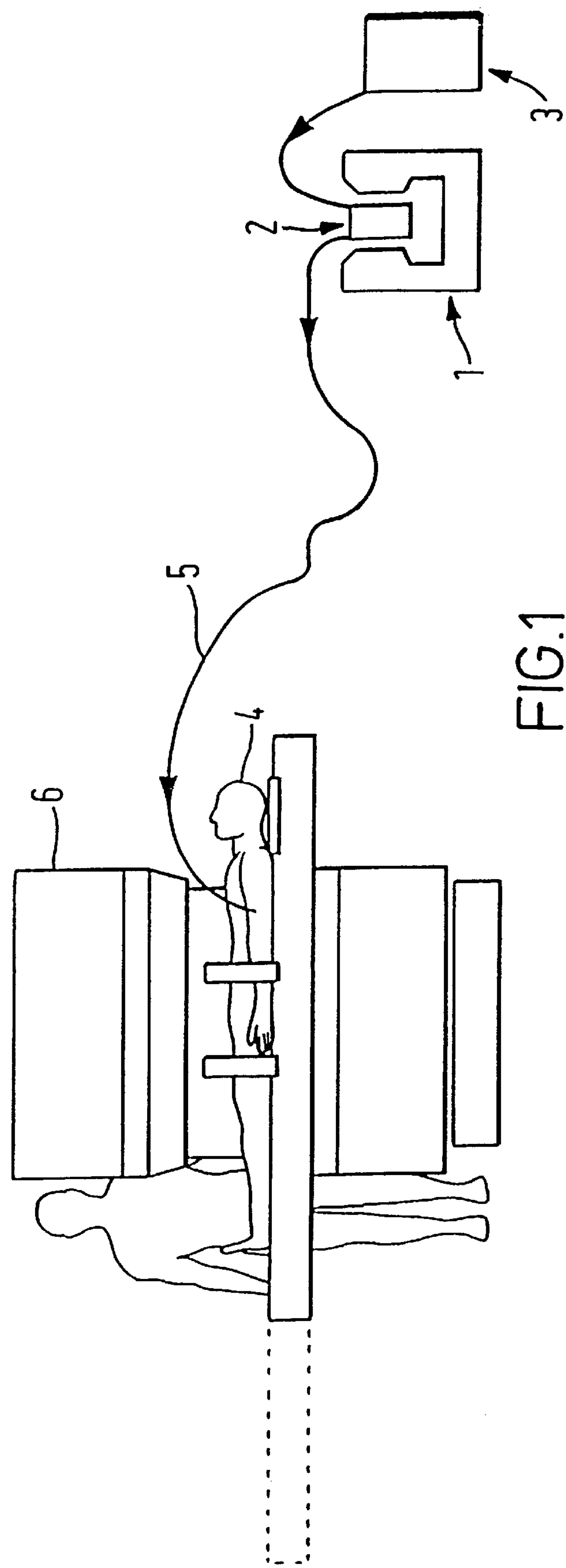
FIG. 1 of the accompanying drawings is a schematic representation of an apparatus suitable for carrying out the invention.

Suitable high $T_1$ agents may contain nuclei such as protons. However other non-zero nuclear spin nuclei may be useful (eg $^{19}F$, $^{3}Li$, $^{1}H$, $^{13}C$, $^{15}N$ or $^{31}P$) and $^{19}F$ and $^{13}C$ nuclei are particularly preferred. In this event the MR signals from which the image is generated will be substantially only from the high $T_1$ agent itself. Nonetheless, where the polarised high $T_1$ agent is present in high concentration in administrable media (eg water), there may be significant enough transfer of magnetisation to the water protons to be able to perform $^1$H-MRI on the water protons of the media. Similarly, the polarised high $T_1$ agent may have a significant enough effect on in vivo water protons for conventional $^1$H MRI to be carried out on those protons.

Where the MR imaging nuclei is other than a proton (eg $^{13}$C or $^{19}$F), there will be essentially no interference from background signals (the natural abundance of $^{13}$C and $^{19}$F being negible) and image contrast will be advantageously high. This is especially true where the high $T_1$ agent itself is enriched above natural abundance. Thus the method according to the invention has the benefit of being able to provide significant spatial weighting to a generated image. In effect, the administration of a polarised high $T_1$ agent to a selected region of a sample (eg by injection) means that the contrast effect may be localised to that region. The precise effect of course depends on the extent of biodistribution over the period in which the high $T_1$ agent remains significantly polarised. In general, specific body volumes (i.e. regions of interest such as the vascular system or specific organs such as the brain, kidney, heart or liver) into which the agent is administered may be defined with improved signal to noise (particularly improved contrast to noise) properties of the resulting images in these volumes.

In one embodiment, a "native image" of the sample (e.g. body) (ie. one obtained prior to administration of the high $T_1$ agent or one obtained for the administered high $T_1$ agent without prior polarisation as in a conventional MR experiment) may be generated to provide structural (eg. anatomical) information upon which the image obtained in the method according to the invention may be superimposed. A "native image" is generally not available where $^{13}$C or $^{19}$F is the imaging nucleus because of the low abundance of $^{13}$C and $^{19}$F in the body. In this case, a proton MR image may be taken to provide the anatomical information upon which the $^{13}$C or $^{19}$F image may be superimposed.

Whilst the high $T_1$ agent may in general be solid, liquid or gas, it should of course by physiologically tolerable or be capable of being provided in a physiologically tolerable, administerable form. Preferred high $T_1$ agents are soluble in aqueous media (eg. water) and are of course non-toxic where the intended end use is in vivo.

Conveniently, the high $T_1$ agent once polarised will remain so for a period sufficiently long to allow the imaging procedure to be carried out in a comfortable time span. Generally sufficient polarisation will be retained by the high $T_1$ agent in its administerable form (eg. in injection solution) if it has a $T_1$ value (at a field strength of 0.01–5 T and a temperature in the range 20–40° C.) of at least 2 s, preferably at least 5 s, more preferably at least 10 s, especially preferably 30 s or longer, more especially perferably 70 s or more, yet more especially preferably 100 s or more (for example at 37° C. in water at 1 T and a concentraion of at least 1 mM). The high $T_1$ agent may be advantageously an agent with a long $T_2$ relaxation time.

The long $T_1$ relaxation time of certain $^{13}$C nuclei is particularly advantageous and certain high $T_1$ agents containing $^{13}$C nuclei are therfore preferred for use in the present method. The γ-factor of carbon is about ¼ of the γ-factor for hydrogen resulting in a Larmor frequency of about 10 MHz at 1 T. The rf-absorption and reflections in a patient is consequently and advantageously less than in water (proton) imaging. Preferably the polarised high $T_1$ agent has an effective $^{13}$C nuclear polarisation corresponding to the one obtained at thermal equilibrium at 300 K in a field of 0.1 T or more, more preferably 25 T or more, particularly preferably 100 T or more, especially preferably 5000 T or more (for example 50 kT). High $T_1$ agents containing $^{19}$F nuclei are also preferred.

When the electron cloud of a given molecule interacts with atoms in surrounding tissue, the shielding of the atom responsible for the the MR signal is changed giving rise to a shift in the MR frequency ("the chemical shift effect"). When the molecule is metabolised, the chemical shift will be changed and high $T_1$ agents in different chemical surroundings may be visualised separately using pulses sensitive to chemical shift. When the frequency difference between high $T_1$ molecules in different surroundings is 150 Hz or higher (corresponding to 3.5 ppm or higher at 1 T), the two components may be excited separately and visualised in two images. Standard chemical shift selective excitation pulses may then be utilised. When the frequency separation is less, the two components may not be separated by using frequency selective rf-pulses. The phase difference created during the time delay after the excitation pulse and before the detection of the MR signal may then be used to separate the two components. Phase sensitive imaging pulse sequence methods (Dixon, Radiology, 1984, 153: 189–194 and Sepponen, Mag Res. Imaging, 3, 163–167, 1985) may be used to generate images visualising different chemical surroundings or different metabolites. The long $T_2$ relaxation time which may be a characteristic of a high $T_1$ agent will under these circumstances make it possible to use long echo times (TE) and still get a high signal to noise ratio. Thus an important advantage of the high $T_1$ agents used in the present method is that they exhibit a chemical shift dependent on the local composition of the body in which they are localised. Preferred high $T_1$ agents will exhibit (at 1 T) a chemical shift of more than 2 ppm, preferably more than 10 ppm depending on whether the high $T_1$ agent is localised inside or outside the vascular system. High $T_1$ agents containing polarised $^{13}$C nuclei (or $^{19}$F nuclei) exhibit large changes in chemical shift in response to physiological changes (eg. pH, $pO_2$, $pCO_2$, redox potential, temperature or ionic concentrations of for example $Na^+$, $K^+$, $Ca^{2+}$) or metabolic activity and therefore may be used to monitor these parameters.

Solid high $T_1$ agents (e.g. $^{13}$C or $^{19}$F enriched solids) may exhibit very long $T_1$ relaxation times and for this reason are especially preferred for use in the present method. The $T_1$ relaxation time may be several hours in the bulk phase, although this may be reduced by reduction of grain size and/or addition of paramagnetic impurities eg. molecular oxygen. The long relaxation time of solids advantageously allows the procedure to be conveniently carried out with less haste and is particularly advantageous in allowing the polarised solid high $T_1$ agent to be stored or transported prior to pharmaceutical formulation and administration. In one embodiment, the polarised high $T_1$ agent may be stored at low temperature eg in frozen form and prior to administration, the high $T_1$ agent may be rapidly warmed to physiological temperatures using conventional techniques such as infrared or microwave radiation or simply by adding hot, sterile administrable media eg saline.

For in vivo use, a polarised solid high $T_1$ agent may be dissolved in administrable media (eg water or saline), administered to a subject and conventional MR imaging performed. Thus solid high $T_1$ agents are preferably rapidly soluble (eg. water soluble) to assist in formulating administrable media. Preferably the high $T_1$ agent should dissolve in a physiologically tolerable carrier (eg water or Ringers solution) to a concentration of at least 1 mM at a rate of 1 mM/3 $T_1$ or more, particularly preferably 1 mM/2 $T_1$ or more, especially preferably 1 mM/$T_1$ or more. Where the solid high $T_1$ agent is frozen, the adminstrable medium may be heated, preferably to an extent such that the temperature of the medium after mixing is close to 37° C.

A polarised high $T_1$ agent may be administered (either alone or with additional components such as additional high $T_1$ agents) in liquid form. The retention of polarisation in a liquid medium vis-a-vis a gas medium is significantly greater. Thus while $T_1$ and $T_2$ are in general shorter for the liquid, the $T_2$* effect due to diffusion is $10^5$ times less significant for the liquid. Consequently for gaseous high $T_1$ agents the imaging sequence used generally has to be FLASH or GRASS while in contrast, more efficient imaging sequences may be used for liquids. For example, liquids generally have slower diffusion which makes it possible to use sequences such as echo planar imaging (EPI). The overall technique will be faster and yield better resolution (voxel size<1 mm) than conventional techniques (voxel size approx. 1–5 mm) at current acquisition times. It will give good images at all fields including in low field (eg. 0.01–0.5 T) machines.

Given that the method of the invention should be carried out within the time that the high $T_1$ agent remains significantly polarised, it is desirable for administration of the polarised high $T_1$ agent to be effected rapidly and for the MR measurement to follow shortly thereafter. The preferred administration route for the polarised high $T_1$ agent is parental eg by bolus injection, by intravenous, intraarterial or peroral injection. The injection time should be equivalent to 5 $T_1$ or less, preferably 3 $T_1$ or less, particularly preferably $T_1$ or less, especially 0.1 $T_1$ or less. The lungs may be imaged by spray, eg by aerosol spray.

The high $T_1$ agent should be preferably enriched with nuclei (eg. $^{19}$F and/or $^{13}$C nuclei) having a long $T_1$ relaxation time. Preferred are $^{13}$C enriched high $T_1$ agents having $^{13}$C at one particular position (or more than one particular position) in an amount in excess of the natural abundance ie above about 1%. Preferably such a single carbon position will have 5% or more $^{13}$C, particularly preferably 10% or more, especially preferably 25% or more, more especially preferably 50% or more, even more preferably in excess of 99% (e.g. 99.9%). The $^{13}$C nuclei should preferably amount to >2% of all carbon atoms in the compound. The high $T_1$ agent is preferably $^{13}$C enriched at one or more carbonyl or quarternary carbon positions, given that a $^{13}$C nuceus in a carbonyl group or in certain quarternary carbons may have a $T_1$ relaxation time typically of more than 2 s, preferably more than 5 s, especially preferably more than 30 s. Preferably the $^{13}$C enriched compound should be deuterium labelled, especially adjacent the $^{13}$C nucleus.

Preferred $^{13}$C enriched compounds are those in which the $^{13}$C nucleus is surronded by one or more non-MR active nuclei such as O, S, C or a double bond. Specifically preferred $^{13}$C enriched agents are $^{13}CO_3^{2-}$ and $H^{13}CO_3^-$ (sodium salt for injection and calcium or potassium salt for polarisation).

Also preferred are the following types of compound (* denotes $^{13}$C enriched positions):

(1) carboxyl compounds comprising 1 to 4 carboxyl groups:

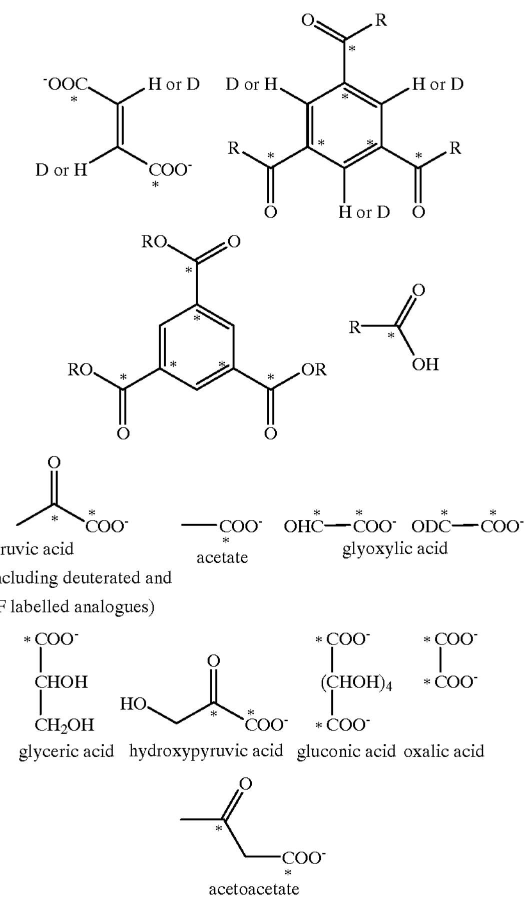

(wherein R represents any straight or branched chain hydrocarbon moiety, preferably a highly substituted carbon atom, especially preferably a quaternary carbon) and esters, isomers, especially stereoisomers and rotamers, thereof:

(2) substituted mono and biaryl compounds:

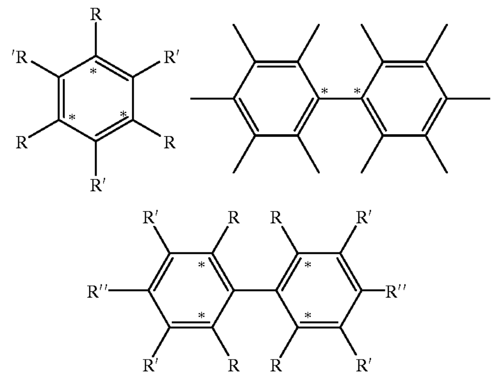

-continued

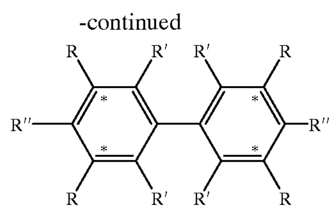

(wherein each group R or R' is independently a hydrogen atom, an iodine atom, a $^{19}F$ atom or a hydrophilic moiety M being any of the non-ionizing groups conventionally used to enhance water solubility within the field of triiodophenyl X-ray contrast agnets including for example a straight chain or branched $C_{1-10}$-alkyl group, preferably a $C_{1-5}$ group, optionally with one or more $CH_2$ or CH moieties replaced by oxygen or nitrogen atoms and optionally substituted by one or more groups selected from oxo, hydroxy, amino, carboxyl derivative, and oxo substituted sulphur and phosporus atoms).

Particular examples of group M include polyhydroxyalkyl, hydroxyalkoxyalkyl and hydroxypolyalkoxyalkyl and such groups attached to the phenyl group via an amide linkage such as hydroxyalkylaminocarbonyl, N-alkyl-hydroxyalkylaminocarbonyl and bis-hydroxyalkylaminocarbonyl groups. Preferred among such M groups are those containing 1, 2, 3, 4, 5 or 6, especially 1, 2 or 3, hydroxy groups, e.g.

—CONH—$CH_2CH_2OH$

—CONH—$CH_2CHOHCH_2OH$

—CONH—$CH(CH_2OH)_2$

—$CON(CH_2CH_2OH)_2$ as well as other groups such as

—$CONH_2$

—$CONHCH_3$

—$OCOCH_3$

—$N(COCH_3)H$

—$N(COCH_3)C_{1-3}$-alkyl

—$N(COCH_3)$-mono, bis or tris-hydroxy $C_{1-4}$-alkyl

—$N(COCH_2OH)$-mono, bis or tris-hydroxy $C_{1-4}$-alkyl

—$N(COCH_2OH)_2$

—$CON(CH_2CHOHCH_2OH)(CH_2CH_2OH)$

—CONH—$C(CH_2OH)_3$ and

—CONH—$CH(CH_2OH)(CHOHCH_2OH)$.

In general, the M groups will preferably each comprise a polyhydroxy $C_{1-4}$-alkyl group, such as $C_{1-4}$-alkyl groups substituted by 1, 2, 3 or 4 hydroxy groups (e.g. hydroxymethyl, 2-hydroxyethyl, 2,3-bishydroxy-propyl, 1,3-bishydroxyprop-2-yl, 2,3,4-trihydroxybutyl, and 1,2,4-trihydroxybut-2-yl) optionally connected to the phenyl ring via a CO, SO or $SO_2$ group (e.g. $COCH_2OH$ or $SO_2CH_2OH$).

Preferred compounds are those in which two or three non-adjacent R groups in the or each $C_6R_5$ moiety are iodine and at least one, and preferably two or three, R groups in the or each $C_6R_5$ moiety are M or $M_1$ moieties; each M independently is a non-ionic hydrophilic moiety; and each $M_1$ independently represents a $C_{1-4}$-alkyl group substituted by at least one hydroxyl group and optionally linked to the phenyl ring via a cabonyl, suphone or sulphoxide group, at least one R group, preferably at least two R groups and especially preferably at least one R group in the or each $C_6R_5$ moiety, being an $M_1$ moiety. Especially preferred are the compounds disclosed in WO-A-96/09282.

(3) sugars:

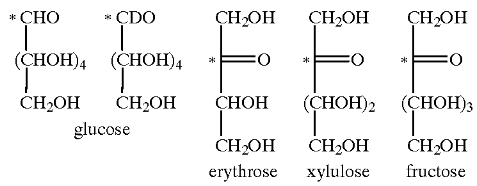

(4) ketones:

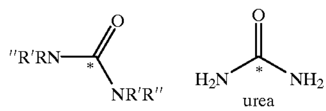

(wherein R and R' are as defined above)

(5) ureas:

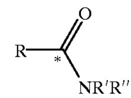

(6) amides:

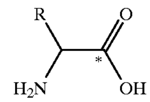

(7) amino acids:

peptides and proteins labelled in the carbonyl position, particularly those known in the art to be useful for targetting tumour cells. Of the proteins, albumin is especially preferred. Polymers are also useful, particularly those with low toxicity (eg polylysine) and those with many carboxyl groups (eg polyglytamic acid). The following amino acids are especially preferred:

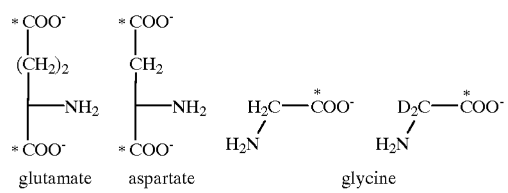

(8) carbonates:

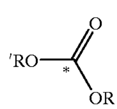

(9) nucleotides:

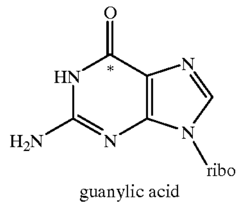

guanylic acid

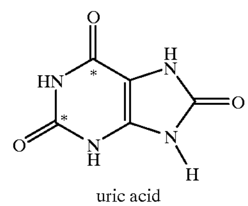

uric acid

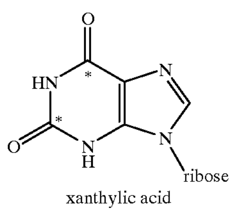

xanthylic acid

(10) tracers:

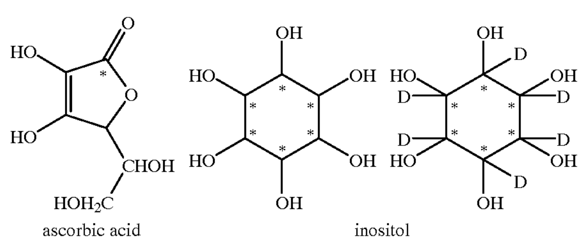

thyroxine

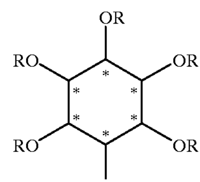

ascorbic acid

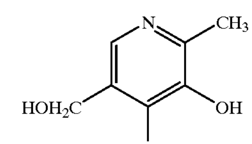

inositol inositolhexanicotinate (hexanicit, Astra)

pyridoxine

R =

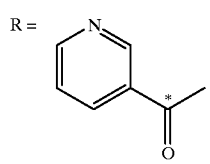

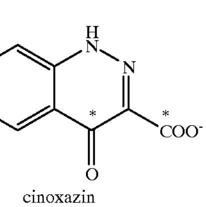

cinoxazin

-continued

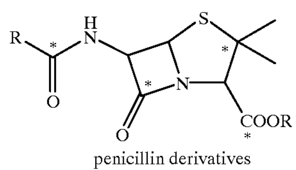

penicillin derivatives

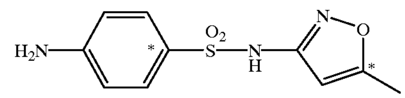

Sulfonamide

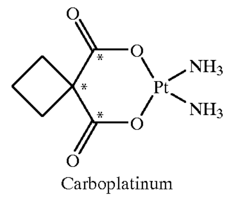

Carboplatinum

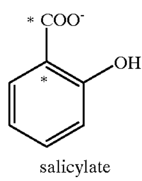

salicylate

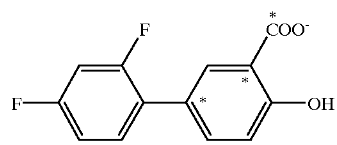

difunisal

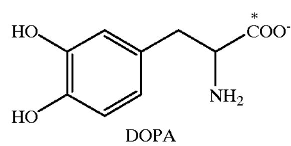

DOPA and (11) compounds such as:

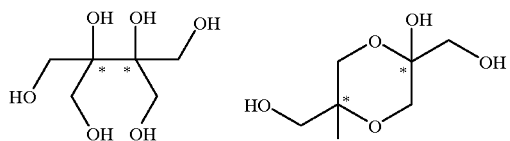

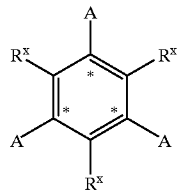

(wherein $R^x$ denotes any of the conventional side chains suitable for use in X-ray contrast agents and A denotes I, D, OR, RC═O or $^{19}F$)

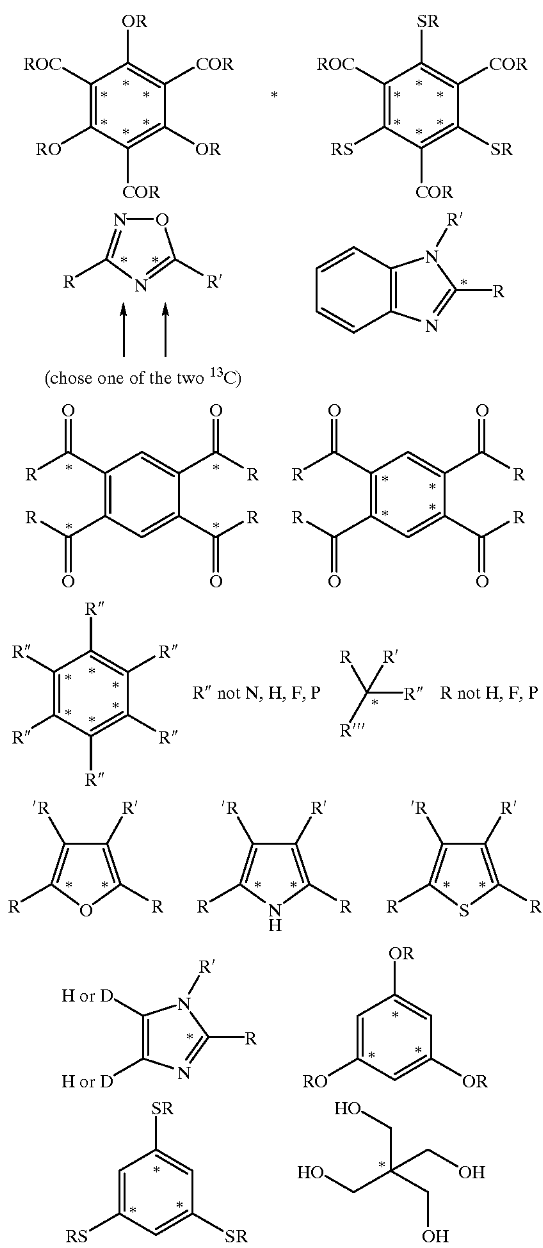

In any of the above definitions, useless otherwise specified R, R', R" and R"' denote any suitable substituent, preferably a substituent bound by a non-magnetic nucleus.

The partly or wholly deuterated or $^{19}$F analogues of any of these compounds are particularly preferred.

Certain of the above-mentioned $^{13}$C enriched compounds are novel per se and form a further aspect of the invention. Compounds which are water soluble are particularly preferred.

In general, $^{13}$C enriched amino acids and any known contrast agents from the fields of X-ray contrast agents and MRI contrast agents (the chelating agent without the metal counterion eg conventional Gd chelating agents without Gd) are preferred as high $T_1$ agents. Intermediates in normal metalbolic cycles such as the citric acid cycle eg. fumaric acid and pyruvic acid are preferred for the imaging of metabolic activity.

$T_1$ values for $^{13}$C enriched compounds useful in the invention are reported in the literature or may be routinely determined. Examples include:

(a) non-water soluble (i.e. soluble in an organic solvent)

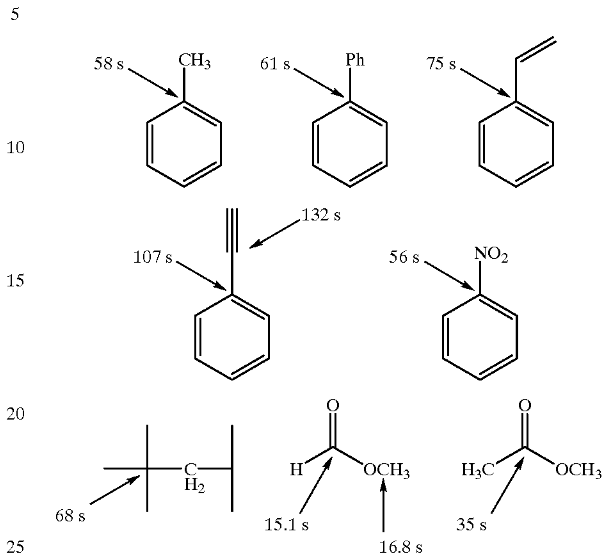

(b) water soluble

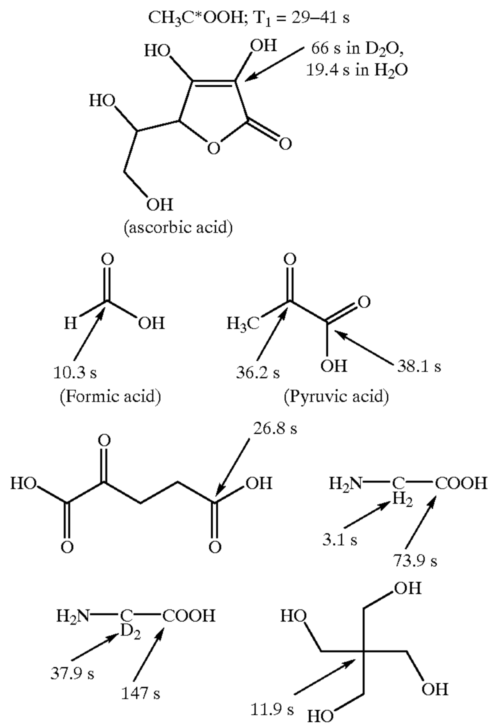

Ex vivo polarisation may be carried out by any known method and by way of example four such methods are described hereinbelow. It is envisaged that, in the method according to the invention, the level of polarisation achieved should be sufficient to allow the high $T_1$ agent to achieve a diagnostically effective contrast enhancement in the sample to which it is subsequently administered in whatever form. In general, it is desirable to achieve a level of polarisation which is at least a factor of 2 or more above the field in which MRI is performed, preferably a factor of 10 or more, particularly preferably 100 or more and especially preferably 1000 or more, eg. 50 kT.

In a first embodiment of the method according to the invention, ex vivo polarisation of the MR imaging nuclei is effected by an OMRI contrast agent. In this embodiment, step (i) of the method comprises:

(a) bringing an OMRI contrast agent and a high $T_1$ agent into contact in a uniform magnetic field (the primary magnetic field $B_o$); and (b) exposing said OMRI contrast agent to a first radiation of a frequency selected to excite electron spin transitions in said OMRI contrast agent.

It is preferred that the OMRI contrast agent and high $T_1$ agent are present as a composition during polarisation.

Dynamic nuclear polarisation tray be attained by three possible mechanisms: (1) the Overhauser effect, (2) the solid effect and (3) thermal mixing effect (see A. Abragam and M. Goldman, Nuclear Magnetism: order and disorder, oxford University Press, 1982). The Overhauser effect is a relaxation driven process that occurs when the electron-nucleus interaction is time-dependent (due to thermal motion or relaxation effects) on the time scale of the inverse electron Larmor frequency or shorter. Electron-nuclear cross-relaxation results in an exchange of energy with the lattice giving rise to an enhanced nuclear polarisation. The overall enhancement depends on the relative strength of the scalar and dipolar electron-nuclear interaction and the microwave power. For statis systems both thermal mixing and the solid effect are operative. In the solid effect, the electron spin system is irradiated at a frequency that corresponds to the sum or difference of the electronic and nuclear Larmor frequencies. The nuclear Zeeman reservoir absorbs or emits the energy difference and its spin temperature is modified, resulting in an enhanced nuclear polarisation. The efficiency depends on the transition probabilities of otherwise forbidden transitions that are allowed due to the mixing of nuclear states by non-secular terms of the electron-nuclear dipolar interaction. Thermal mixing arises when the electron-electron dipolar reservoir establishes thermal contact with the nuclear Zeeman reservoirs This takes place when the characteristic electronic resonance line width is of the order of the nuclear Larmor frequency. Electron-electron cross relaxation between spins with difference in energy equal to the nuclear Zeeman energy is absorbed or emitted by the electronic dipolar reservoir, changing its spin temperature and the nuclear polarisation is enhanced. For thermal mixing both the forbidden and the allowed transitions can be involved.

In the first embodiment where the polarising agent is an OMRI contrast agent, the method may be conveniently carried out by using a first magnet for providing the polarising magnetic field and a second magnet for providing the primary magnetic field for MR imaging. The same magnet could be used for both purposes. FIG. 1 of the accompanying drawings is a schematic representation of an apparatus suitable for carrying out the first embodiment of the invention. A freestanding polarising magnet (1) optionally together with a filter surrounds an EPR resonator (2) which provides the nuclear polarisation. A container (3) comprising a pump is provided for carrying out the contrast composition which is delivered to a subject (4) by a delivery line (5). The subject is situated within a conventional MR scanner (6).

Figure 2:
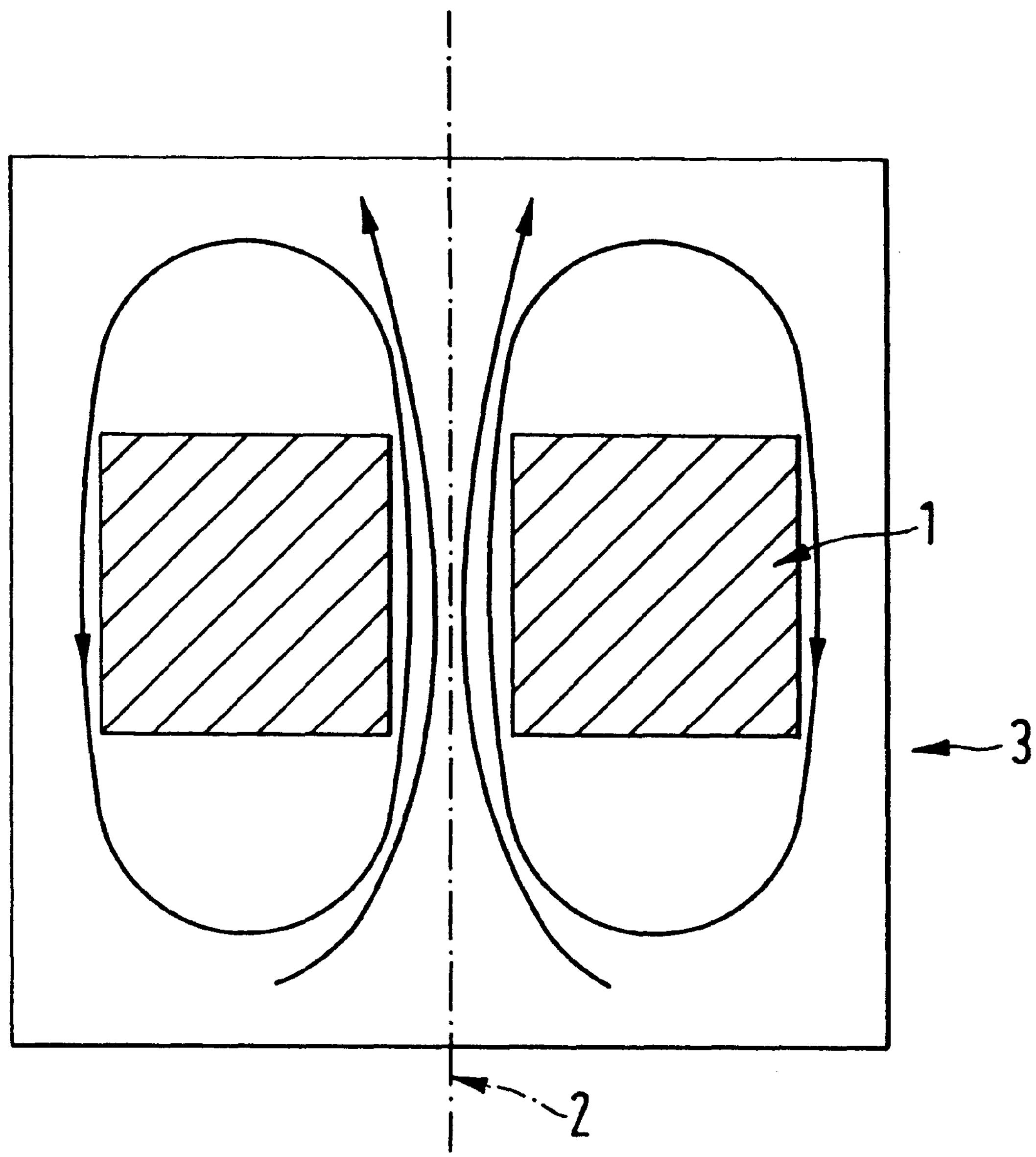
FIG. 2 of the accompanying drawings shows a dielectric resonator within a metal box.

In the above apparatus, a dielectric resonator may be used in the dynamic nuclear polarisation process. Generally speaking, dynamic nuclear polarisation requires a volume with a fairly strong high frequency magnetic field and an accompanying electric field which is made as small as possible. A dielectric resonator may be used to provide a preferred field arrangement in which the magnetic field lines are shaped like a straw in a sheaf of corn with an electric field forming circles like the thread binding the sheaf. A field arrangement of this type may be formed by one of several rings or tubes of a material with a high dielectric constant and low loss. The man skilled in the art will appreciate that such a tube will exhibit different electromagnetic resonant modes. One of the dominant modes has the desired characteristic of electric field circulating around the tube axis within the wall and being zero at the axis and everywhere perpendicular to it. The magnetic field on the other hand is concentrated around the tube axis and mainly directed along it. The composition to be polarised is conveniently placed inside the resonator which is itself placed inside a metal box with a clearance typically of the order of the size of the resonator, and is excited to the desired resonance with a coupling loop or the like. The metal box ensures that the electromagnetic energy does not leak away by radiation. FIG. 2 of the accompanying drawings shows a dielectric resonator (1) (with an axis of rotational symmetry (2)) within a metal box (3).

An alternative to the dielectric resonator is a resonant cavity of Which several are known to those skilled in the art. One simple and efficient resonant cavity is a metal box, such as a cylindrical metal box. A suitable mode is the one known as TM1,1,0 which produces a perpendicular magnetic field on the axis of the cavity. It is possible to excite two such modes in the same cavity at the same frequency producing fields which are mutually perpendicular. By arranging them to have a 90° phase difference a rotating field can be produced which is especially efficient for implementing dynamic polarisation with a minimum of dissipation in the sample. Modes with similar field distributions for different shapes of cavities e.g. rectangular cavities are familiar to those skilled in the art.

The composition may also be dispersed into a plurality of compartments during the dynamic nuclear polarisation step. Thus the composition might be typically divided into parallel channels provided, for example, by parallel separating plates, discs or tubes, typically open-ended tubes. The electric losses (eddy currents) in the composition caused by the magnetic field are decreased by dividing the composition into smaller volumes using electrically isolating barriers, preferably situated perpendicular to the field. If the composition is in a cylindrical vessel surrounded by a dielectric resonator as described hereinbefore, the isolating barriers would be planes passing radially from the vessel axis to its wall. A simpler and more practical arrangement is to polarise the composition in a container which contains a plurality of thin-walled tubes of an isolating material such as quartz, glass or plastic. This has the advantage of reducing the electric losses in the composition which allows a larger volume of composition to be polarised for the same applied electromagnetic power. The walls, the inner, outer or both of the tubes may similarly serve as the substrate onto which the OMRI contrast agent is bound so that pressure applied to one end of the container may force the polarized, substantially OMRI contrast agent free, fluid high $T_1$ agent from the container, for example with a delivery line leading to the subject (patient) undergoing MR examination.

It is envisaged that in the first embodiment of the method according to the invention, use may be made of any known OMRI contrast agent capable of polarising a high $T_1$ agent to an extent such that a diagnostically effective contrast enhancement, in the sample to which the high $T_1$ agent is administered, is achieved. Where the OMRI contrast agent is a paramagnetic free radical, the radical may be conveniently prepared in situ from a stable radical precursor by a conventional physical or chemical radical generation step shortly before polarisation. This is particularly important where the radical has a short half-life. In these cases, the radical will normally be non-reusable and may conveniently be discarded once the separation step of the method according to the invention has been completed.

In solids, it is preferred to effect dynamic nuclear polarisation by irradiating an electron spin at low temperature and high field. Specific examples of dynamic nuclear polarisation of solid high $T_1$ agents are:

(1) 15N-Ala labelled T4-lysosome and 13C-Glycine in frozen aqueous solutions of 60:40 glycerol/water with the free radical 4-amino TEMPO as the source of electron polarisation (D. A. Hall, D. Maus, G. Gerfen and R. G. Griffin, Science, 19–97), Enhancements of ca.50 and 100 were obtained, respectively, at 5T and 40K;

(2) Carboxy-13C labelled glycine in frozen aqueous solution of 60:40 glycerol/water with TEMPO as the free radical. An enhancement of 185 at 5T and 14K was obtained (G. J. Gerfen, L. R. Becerral D. A. Hall, R. G. Griffin, R. J, Temkin, D. J. Singel, J. Chem. Phys. 102(24), 9494–9497 (1995);

(3) Dynamic polarisation of protons and deuterons in 1,2-athanedial doped with complexes of Cr at 2.5T. The obtained degree of polarisation is 80% (W. De Boer and T. O Niinikoski, Nuol. Instrum. Meth. 114, 495 (1974). Preferably of course a chosen OMRI contrast agent will exhibit a long half-life (preferably at least one hour), long relaxation times ($T_{1e}$ and $T_{2e}$), high relaxivity and a small number of ESR transition lines. Thus the paramagnetic oxygen-based, sulphur-based or carbon-based organic free radicals or magnetic particles, referred to in WO-A-68/10419, WO-A-90/00904, WO-A-91/12024, WO-A-93/02711 or WO-A-96/39367 would be suitable OMRI contrast agents. A particularly preferred characteristic of a chosen OMRI contrast agent is that it exhibits low inherent ESR linewidths, preferably less than 500 mG, particularly preferably less than 400 mG, especially preferably less than 150 mG. Generally speaking, organic free radicals such as triarylmethyl and nitroxide radicals provide the most likely source of such desirably low linewidths eg. those described in WO-A-88/10419, WO-A-90/00904, WO-A-91/12024, WO-A-93/02711 or WO-A-96/39367.

However, OMRI contrast agents useful in the first embodiment of the present method are not limited to paramagnetic organic free radicals. Particles exhibiting the magnetic properties of paramagnetism, superparamagnetism, ferromagnetism or ferrimagnetism may also be useful OMRI contrast agents, as may be other particles having associated free electrons. Superparamagnatic nanoparticles (eg. iron or iron oxide nanoparticies) may be particularly useful. Magnetic particles have the advantages over organic free radicals of high stability and a strong electronic/nuclear spin coupling (ie. high relaxivity) leading to greater Overhauser enhancement factors.

For the purposes of administration, the high $T_1$ agent should be preferably administered in the absence of the whole of, or substantially the whole of, the OMRI contrast agent. Preferably at least 80% of the OMRI contrast agent is removed, particularly preferably 90% or more, especially preferably 95% or more, most especially 99% or more. In general, it is desirable to remove as much OMRI contrast agent as possible prior to administration to improve physiological tolerability and to increase $T_1$. Thus preferred OMRI contrast agents for use in the first embodiment of the method according to the invention are those which can be conveniently and rapidly separated from the polarised high $T_1$ MR imaging agent using known techniques as discussed below. However where the OMRI contrast agent is non-toxic, the separation step may be omitted. A solid (eg. frozen) composition comprising an OMRI contrast agent and a high $T_1$ agent which has been subjected to polarisation may be rapidly dissolved in saline (eg. warm saline) and the mixture injected shortly thereafter.

In the separation step of the first embodiment of the method of the invention, it is desirable to remove substantially the whole of the OMRI contrast agent from the composition (or at least to reduce it to physiologically tolerable levels) as rapidly as possible. Many physical and chemical separation or extraction techniques are known in the art and may be employed to effect rapid and efficient separation of the OMRI contrast agent and high $T_1$ agent. Clearly the more preferred separation techniques are those which can be effected rapidly and particularly those which allow separation in less than one second. In this respect, magnetic particles (eg. superparamagnetic particles) may be advantageously used as the OMRI contrast agent as it will be possible to make use of the inherent magnetic properties of the particles to achieve rapid separation by known techniques. Similarly, where the OMRI contrast agent or the particle is bound to a solid bead, it may be conveniently separated from the liquid (i.e. if the solid bead is magnetic by an appropriately applied magnetic field).

for ease of separation of the OMRI contrast agent and the high $T_1$ agent, it is particularly preferred that the combination of the two be a heterogeneous system, eg. a two phase liquid, a solid in liquid suspension or a relatively high surface area solid substrate within a liquid, eg. a solid in the form of beads fibres or sheets disposed within a liquid phase high $T_1$ agent. In all cases, the diffusion distance between the high $T_1$ agent and OMRI contrast agent must be small enough to achieve an effective Overhauser enhancement. Certain OMRI contrast agents are inherently particulate in nature, eg. the paramagnetic particles and superparamagnetic agents referred to above. Others may be immobilized on, absorbed in or coupled to a solid substrate or support (eg. an organic polymer or inorganic matrix such as a zeolite or a silicon material) by conventional means. Strong covalent binding between OMRI contrast agent and solid substrate or support will, in general, limit the effectiveness of the agent in achieving the desired Overhauser effect and so it is preferred that the binding, if any, between the OMRI contrast agent and the solid support or substrate is weak so that the OMRI contrast agent is still capable of free rotation. The OMRI contrast agent may be bound or to the to a water insoluble substrate/support prior to the polarisation or the OMRI contrast agent may be attached/bound to the substrate/support after polarisation. The OMRI contrast agent may then be separated from the high $T_1$ agent e.g. by filtration before administration. The OMRI contrast agent may also be bound to a water soluble macromolecule and the OMRI contrast agent-macromolecule may be separated from the high $T_1$ agent before administration.

Where the combination of an OMRI contrast agent and high $T_1$ agent is a heterogeneous system, it will be possible to use the different physical properties of the phases to carry out separation by conventional techniques. For example, where one phase is aqueous and the other non-aqueous (solid or liquid) it may be possible to simply decant one phase from the other. Alternatively, where the OMRI contrast agent is a solid or solid substrate (eg. a bead) suspended in a liquid high $T_1$ agent the solid may be separated from the liquid by conventional means eg. filtration, gravimetric, chromtographic or centrifugal means. It is also envisaged that the OMRI contrast agents may comprise lipophilic moieties and so be separated from the high $T_1$ agent by passage over or through a fixed lipophilic medium or the OMRI contrast agent may be chemically bound to a lipophilic solid bead. The high $T_1$ agent may also be in a solid (eg. frozen) state during polarisation and in close contact with a solid OMRI contrast agent. After polarisation it may be dissolved in heated water or saline or melted and removed or separated from the OMRI contrast agent where the latter may be toxic and cannot be administered.

One separation technique makes use of a cation exchange polymer and a cationic OMRI contrast agent, eg. a triarylmethyl radical carrying pendant carboxylate groups. Alternatively acidifying the solution to around pH 4 may cause the OMRI contrast agent to precipitate out. Separation may then be carried out for example by filtration followed by neutralisation. An alternative technique involves adding ions which causes precipitation of ionic OMRI agents which may then be filtered off.

Certain OMRI contrast agents, such as the triarylmethyl radical, may have an affinity for proteins. Thus, after polarisation, a composition containing an OMRI contrast agent with a protein affinity may be passed through or over a protein in a form which exposes a large surface area to the agent eg. in particulate or surface bound form. In this way, binding of the OMRI contrast agent to the protein enables it to be removed from the composition.

Alternatively when a hydrophilic high $T_1$ agent is in a solid (eg. frozen) form it may be brought into contact with a hydrophobic OMRI contrast agent which is dissolved in an organic fluid with a melting temperature higher than the high $T_1$ agent. The mixture is frozen and polarisation performed. After polarisation, the mixture is heated and the solid OMRI contrast agent and its solvent are removed. The high $T_1$ agent will remain hyperpolarised for a significant time in the frozen state and may be transported long distances before being dissolved in water or saline for injection.

In a second embodiment of the method according to the invention, ex vivo polarisation of the MR imaging nuclei is effected by para-hydrogen enriched hydrogen gas. Thus step (i) of the second embodiment of the method according to the invention comprises:

(a) preparing enriched hydrogen;

(b) reacting said enriched hydrogen with a hydrogenatable high $T_1$ agent precursor to produce a hydrogenated high $T_1$agent;

Hydrogen molecules exist in two different forms, namely para hydrogen (p-$H_2$) where the nuclear spins are antiparallel and out of phase (the singlet state) and ortho hydrogen (o-$H_2$) where they are parallel or antiparallel and in phase (the triplet state). At room temperature, the two forms exist in equilibrium with a 1:3 ratio of para:ortho hydrogen. At 80K the ratio is 48:52 and at 20K is 99.8:0.2. The rate of equilibration is very low in pure hydrogen but in the presence of any of several known catalysts (such as $Fe_3O_4$ or activated charcoal) an equilibrium mixture is rapidly obtained and remains stable at room temperature for several hours after liberation from the catalyst. Thus by "enriched hydrogen" above is meant hydrogen in which there is a higher than equilibrium proportion of para-hydrogen, for example more than 25%, preferably 45% or more, more preferably 60% or more, particularly preferably 90% or more, especially preferably 99% or more. Typically the preparation of enriched hydrogen in step (a) above will be carried out catalityically at low temperatures e.g. at 160K or less, preferably at 80K or less or more preferably at about 20K.

Generally speaking, if a para-hydrogen molecule is transferred to a high $T_1$ precursor molecule by means of catalytic hydrogenation (typically at elevated pressure (e.g. 50 to 100 bar)), the proton spins remain antiparallel and begin to relax to thermal equilibrium with the normal time constant $T_1$ of the hydrogen in the molecule (typically about one second). However during relaxation some of the polarisation may be transferred to neighbouring nuclei by cross-relaxation or other types of coupling. The presence of, for example, a $^{13}C$ nucleus with a suitable substitution pattern close to the relaxing hydrogen may lead to the polarisation being conveniently trapped in the slowly relaxing $^{13}$ C nucleus. An enhancement factor or 2580 has been reported in the literature (Barkemeyer et al, 1995 J Am Chem Soc 117, 2927–2928).

High $T_1$ agent precursors suitable for use in the second embodiment of the present invention are hydrogenatable and will typically possess one or more unsaturated bonds, e.g. double or triple carbon-carbon bonds. Preferably the high $T_1$ agent precursor may be $^{13}C$ enriched in positions close to the hydrogenation site, e.g. a double or triple bond where relaxation is slow.

Generally speaking, to increase the MR signal from the hydrogenated high $T_1$ agent, it is desirable to incorporate more than one unsaturated bond in each molecule of the hydragenatable high $T_1$ agent precursor, preferably in a conjugated unsaturated system. However due consideration must be given to the need to keep molecular weight relatively low to prevent difficulties in administration of the agent. The presence of one or more acetylene groups in the hydrogenatable high $T_1$ agent precursor increases the reaction rate and is therefore preferred. More preferred are compounds with an unsaturated carbon-carbon bond with one ore more carbonyl substituents, e.g. an $\alpha\beta$ unsaturated carbonly compound. Particularly preferred are compounds comprising disubstituted unsymmetric alkene or acetylene groups with a carbonyl-unsaturation-carbonyl moiety. Such compounds are of high reactivity and may allow two or more $^{13}C$ atoms to be incorporated to utilize the polarisation more efficiently.

Specifically preferred hydrogenatable high $T_1$ agent precursors for use in the second embodiment of the method of the invention include simple acids (e.g. acrylic acid, crotonic acid, propionic acid, furaric acid and maleic acid),

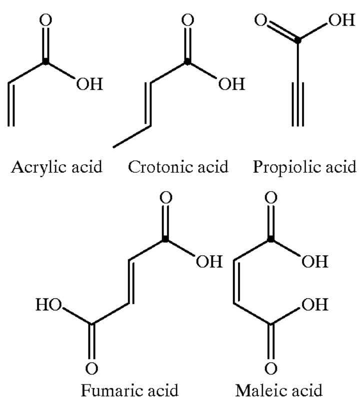

Acrylic acid Crotonic acid Propiolic acid

Fumaric acid Maleic acid quaternary $^{13}C$ containing compounds such as

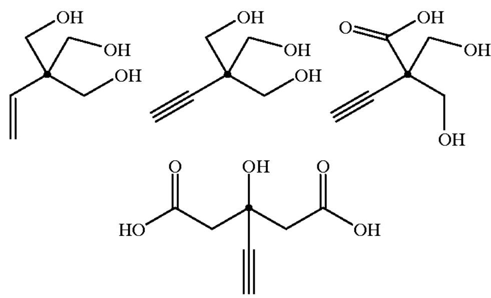

compounds with more than one hydrogenation site such as

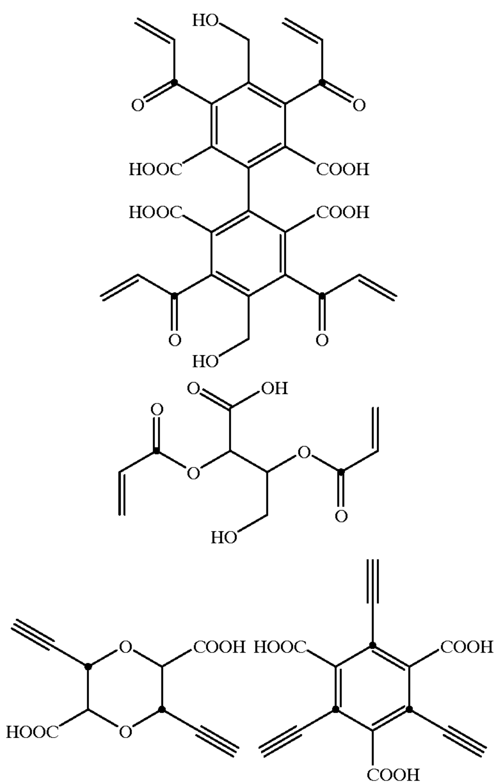

and other compounds such as:

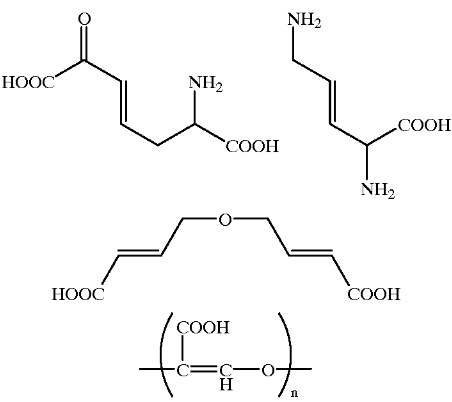

and

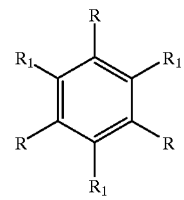

(where $R_1$ is and R is $CONHR_2$ and $R_2$ is a conventional hydrophilic group known to be useful in X-ray contrast media such as one of the examples given hereinbefore)

Due to their biotolerablity, compounds with quaternary carbons are preferred. Cationic compounds may also be used e.g. quaternary ammonium salts.

One especially preferred hydrogenated high $T_1$ agent is maleic acid dimethyl ester which is the hydrogenation product of acetylene dicarboxylic acid dimethyl ester.

Typically the hydragenatable high $T_1$ agent precursor will undergo hydrogenation in the presence of a suitable catalyst, optionally at elevated temperature or pressure. The hydrogenation catalyst need not be a homogeneous catalyst but during hydrogenation the entire hydrogen molecule should be transferred to the host molecule. Some examples of catalysts that are able to fulfil this criterion are shown in Table 1.

TABLE 1

Hydrogenation catalysts that transfer dihydrogen to a double or triple bind

| Catalyst | Synonym | Water Solubility | Comment |
|---|---|---|---|
| $(PPh_3)RhCl$ | Wilkinson's catalyst | – | Active when bound to zeolite (12 Å) |
| $[(NBD)Rh(Amphos)_2]^{3+}$ | | + | Cationic |
| $(TPPMS)_3RhCl$ | | + | Anionic |
| $(HEXNa)_2RhCl$ | | + | Anionic |
| $(OCTNa)_2RhCl$ | | + | Anionic |
| $IrCl(CO)(PPh_3)_2$ | Vasca's complex | – | |

P(Ph)3

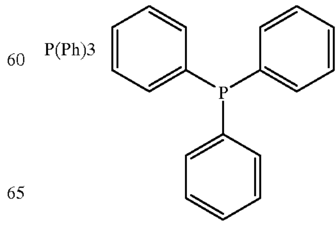

TABLE 1-continued

Hydrogenation catalysts that transfer dihydrogen to a double or triple bind

| Catalyst | Synonym | Water Solubility | Comment |
| --- | --- | --- | --- |
| HEXNa | | | |
| TPPMS | | | |
| OCTNa | | | |
| TPPTS | | | |
| Amphos | | | |

NBD = Norbornadiene

Figure 3:
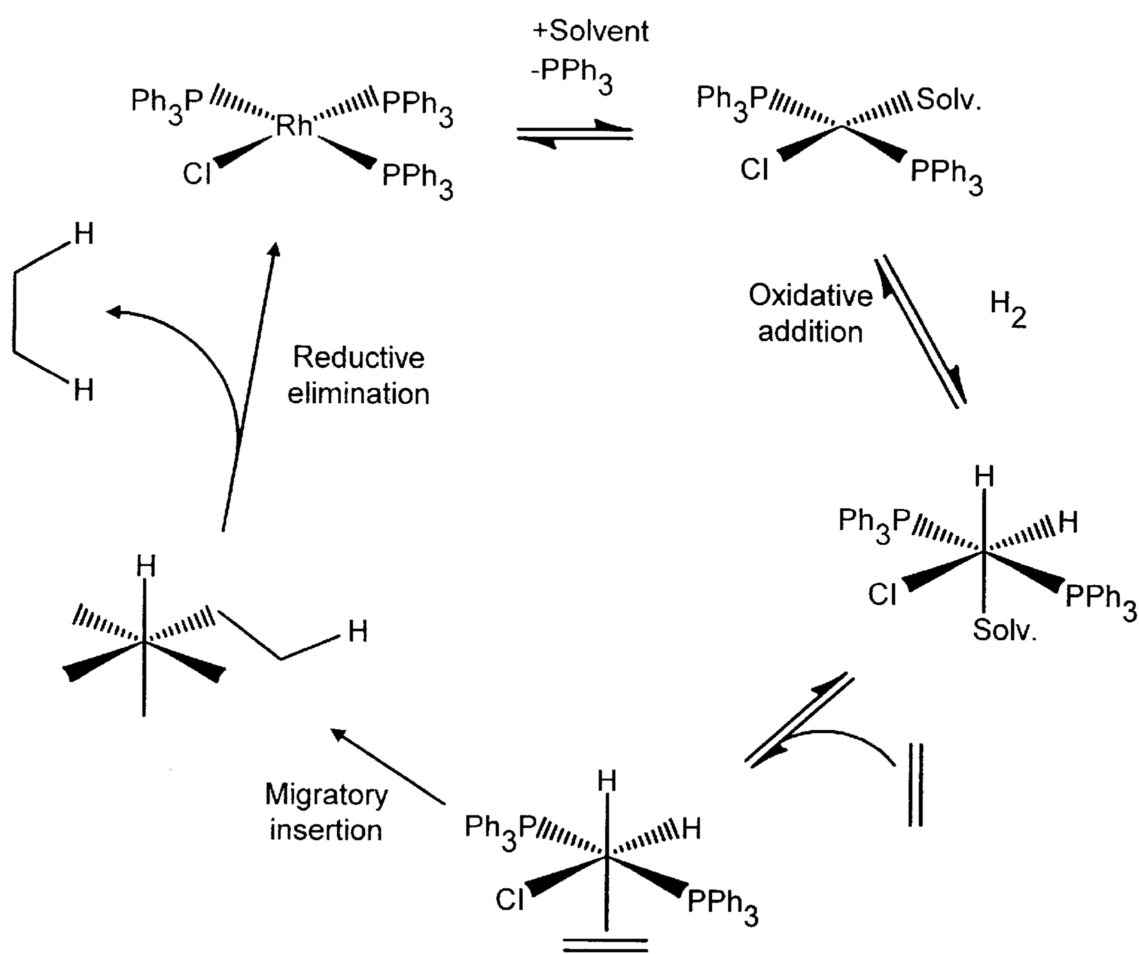
FIG. 3 of the accompanying drawings shows the reaction mechanism of hydrogenation of ethylene with Wilkinson's catalyst.

The reaction mechanism of hydrogenation of ethylene with Wilkinson's catalyst is shown by way of example in FIG. 3. The oxidative addition of enriched hydrogen to the catalyst is generally an equilibrium step which means that certain catalysts will also interconvert p-$H_2$ and o-$H_2$. It is therefore desirable that the chosen hydrogenatable high $T_1$ agent precursor is highly reactive.

Hydrogenation may be conveniently but not necessarily performed in aqueous media and appropriate catalysts for this use should operate efficiently in water and conveniently not facilitate the exchange of hydrogen atoms between water and the enriched hydrogen, otherwise the polarisation is quickly lost. A water soluble rhodium catalyst is one preferred example.

In order to facilitate rapid separation of catalyst and hydrogenated high $T_1$ agent after hydrogenation, the catalyst is preferably one which is immobilized on a solid material e.g. a polymeric material which allows the catalyst-bound solid material to be rapidly filtered off after reaction. Known examples useful for the second embodiment of the present method include catalysts covalently linked to a support or adsorbed on derivatized silica.

An alternative way to remove catalyst from an aqueous solution is to run the reaction in the presence of a water-soluble catalyst (eg a rhodium catalyst) which may then be removed by filtration through an ion-exchange resin or any other sort of filter that can retain the catalyst and allow the product to pass. In the preferred case of a cationic catalyst, filtration may be carried out through a cation exchanger. One such embodiment makes use of an ion-exchange resin bound cationic complex such as $[(NBD)Rh(Amphos)_2]^{3+}$. The aqueous solution of an anionic or neutral product is obtained in the filtrate. The opposite procedure may of course be used for anionic catalysts but these are generally less preferred. A neutral catalyst may be separated from the high $T_2$ agent by making use of physical characteristics such as lipophilicity. For example, a lipophilic catalyst (e.g. Wilkinson's catalyst) may be used in a biphasic system such as water/C18-derivatised silica or even two immiscible liquids such as water/heptane.

Hydrogenation may take place advantageously in a non-aqueous media in which the hydrogenation product is insoluble (ie. from which it precipitates). The increased $T_1$ of the solid high $T_1$ agent allows more time for isolation and subsequent dissolution in an administrable medium. Hydrogenation may also take place with the high $T_1$ agent precursor being insoluble in non-aqueous media but with a particle size as small as possible to increase reactive surface area. The use of non-aqueous media, preferably media with non-magnetically active nuclei (eg. $CS_2$ or $CO_2$ under supercritical conditions) advantageously reduces polarisation loss from the polarised high $T_1$ agent and allows the use of an extended range of catalysts.

In a third embodiment of the method according to the invention, ex vivo polarisation of the nuclei is effected by a hyperpolarisable gas. In this third embodiment, step (i) of the method according to the invention comprises:

(a) hyperpolarising a hyperpolarisable gas before, during or after introducing a high $T_1$ agent thereto whereby to cause nuclear polarization of said high $T_1$ agent.

By hyperpolarisable gas is meant a gas with a non-zero spin angular momentum capable of undergoing an electron transition to an excited electron state and thereafter of decaying back to the ground state. Depending on the transition that is optically pumped and the helicity of the light a positive or negative spin hyperpolarisation may be achieved (up to 100%). Examples of gases suitable for use in the third embodiment of the method of the invention include the noble gases He (eg. $^{3}$He or $^{4}$He) and Xe (eg. $^{129}$Xe), preferably He, particularly preferably $^{3}$He. Alkali metal vapours ay also be used eg. Na, K, Rb, Cs vapours. Mixtures of the gases may also be used or the hyperolarisable gas may be used in liquid or solid form. The term hyperpolarisable gas also covers any gas with non-zero nuclear spin which may be polarised by optical pumping and is preferably $^{129}$Xe or $^{3}$He.

It will be appreciated that in the third embodiment of the invention, the hyperpolarised gas may transfer polarisation to the nuclear spin system of a high $T_1$ agent directly or indirectly. Where the high $T_1$ agent is to be polarised indirectly by water vapour, it may be advantageously water soluble.

For the purposes of polarisation according to the third embodiment of the invention, the high $T_1$ agent may be generally in gaseous, liquid or solid form. One particularly preferred gaseous high $T_1$ agent is water vapour which is conveniently mixed with a hyperpolarisable gas (eg. $^{129}$Xe, $^3$He or $^4$He) at an elevated temperature to maintain the vapour. Generally speaking, the more dense the gaseous mixture, the more rapid is the polarisation transfer to the water vapour so that it is desirable to have the gas mixture under a pressure typically above 3 atmospheres, preferably above 30 atmospheres or even more preferably above 300 atmospheres. Indirect polarisation transfer may be achieved via an intermediate gas medium, for example water vapour.

Where the high $T_1$ agent is polarised whilst in a gaseous state, it is convenient (for the purposes of separation from the hyperpolarised gas and of administration) to be able to rapidly convert it into a liquid or solid. This has the added benefit of significantly increasing $T_1$. Thus where water vapour is used as the high $T_1$ agent, rapid quenching is desirable to condense out polarised water, preferably as ice. Thus removing the elevated pressure and temperature imposed on the gas mixture will lead to rapid cooling and condensation of polarised water. Further rapid cooling is possible by adding, for example, cold saturated salt solutions (eg. Ringers Solution at −15° C.) or other cooling agents. Yet further cooling is possible by, for example, contacting the polarised high $T_1$ agent with a cold surface.

Water vapour may be created in situ by heating a water/hyperpolarisable gas mixture in a suitable chamber. In this case, the inert nature of noble gases is a particular advantage. The volume of water vapour used is generally 5 liters or more, preferably 10 liters or more, particularly preferably 30 liters or more and especially preferably 60 liters or more. In practice, the concentration of noble gas required is relatively low. If the gas has only nuclear magnetism the pressure should be more than 3 atmospheres, preferably 30 atmospheres or more and more preferably 300 atmospheres or more.

In a preferred embodiment, a hyperpolarised fluid eg. $^{129}$Xe at elevated pressure and/or low temperature is passed through a column of solid $^{13}$C enriched and/or $^{19}$F enriched high $T_1$ agent until steady state polarisation of the solid is almost achieved. In general any of the above-mentioned $^{13}$C enriched agents may be used.

In another preferred embodiment, a hyperpolarised gas is frozen/crystallised on the solid/frozen surface of a solid high $T_1$ agent which has been prepared with as large a surface area as possible. The mixture may be transported before warm administrable media (eg. saline) is added and physiological temperature reached before injection.

In order to generate a hyperpolarised gas, the gas is first subjected to a discharge or other means of excitation (eg. an appropriate radiofrequency) which creates a metastable unpaired electron spin state and is then optically (eg. laser) pumped at an appropriate frequency to create electron hyperpolarisation. The various methods for achieving this are well known to those skilled in the art or are described in inter alia U.S. Pat. No. 5,545,396.

Preferred hyperpolarisable gases for use in the third embodiment of the method according to the invention are those which can be conveniently and rapidly separated from the polarised high $T_1$ agent. Noble gases are particularly useful given their very low boiling points and inertness. Preferably the chosen gas will exhibit a long hyperpolarisability half-life (preferably at least 1000s, particularly preferably at least 4000s and especially preferably 8000s or more).

A hyperpolarised gas may, if desired, be stored for extended periods of time in a hyperpolarised state. This is achieved by maintaining the gas at very low temperatures, preferably in a frozen state.

For ease of separation of the hyperpolarisable gas and the high $T_1$ agent, the combination of the two may be advantageously a heterogeneous system, eg. the high $T_1$ agent is a solid or liquid at ambient temperatures. In all cases, the diffusion distance between the high $T_1$ agent and gas, fluid or solid must be small enough to achieve an effective polarisation.

In the separation step of the third embodiment of the method of the invention, it is desirable to remove substantially the whole of the hyperpolarisable gas from the composition (or at least to reduce it to physiologically tolerable levels) as rapidly as possible. If desired, the gas may be reused which may be an important consideration given the expense of noble gases. Many physical and chemical separation or extraction techniques known in the art may be employed to effect rapid and efficient separation of the hyperpolarisable gas and high $T_1$ agent. Clearly the more preferred separation techniques are those which can be effected rapidly and particularly those which allow separation in a fraction of the relaxation time $T_1$ of the high $T_1$ agent.

In a fourth embodiment of the method of the invention, ex vivo nuclear polarisation of the MR imaging nuclei is effected by the use of a high field as described in U.S. Pat. No. 5,479,925 (GEC) and U.S. Pat. No. 5,617,859 (GEC). U.S. Pat. No. 5,479,925 discloses a method for generating MR angiograms in which a contrast agent is passed through a small, high field polarising magnet ex vivo, in order to generate a high longitudinal magnetisation in the agent prior to its administration to the subject. There is however no mention or suggestion of the use of high $T_1$ agents to achieve an improved effect.

Generally speaking, polarisation of an MR imaging nuclei may be achieved by thermodynamic equilibration at low temperature and high magnetic field. Where the contrast medium to be administered is a solid material (e.g. crystalline), it may be introduced into a magnetic field at very low temperature. Under these conditions, $T_1$ is very long (typically many hours or months) and consequently it takes an unacceptably long time for the medium to reach thermodynamic equilibrium. It has however been surprisingly found that, if the contrast medium is exposed to a strong variable magnetic gradient, $T_1$ decreases significantly and thermodynamic equilibrium may be achieved in a more convenient period of time. Thus if the contrast medium undergoes small movements in the gradient field for example by exposure to a magnetic field gradient and ultrasound or by relative movement within the gradient field, $T_1$ will drop. When thermodynamic equilibrium is attained, all nuclei in the contrast medium will be highly polarised relative to room temperature and to normal magnetic fields used in MRI. This procedure has the advantage of allowing the contrast medium to be removed from the magnet and transported in a “ready-to-use” form to the place where it is to be used. Preferably but not essentially transport may take place at a relatively low temperature (e.g. at liquid nitrogen temperature). The $T_1$ of the high $T_1$ solid contrast medium will be long enough to allow transport at ambient temperature before use.

The magnetic field strength used in this fourth embodiment of the invention should be as high as possible, preferably >1 T, more preferably 5 T or more, especially preferably 15 T or more. The temperature should be very low e.g. 100 K or less, preferably 1 K or less, especially preferably 1 mK or less.

Thus viewed from a further aspect the present invention provides a process for preparing polarised high $T_1$ agents, said process comprising:

(i) subjecting a high $T_1$ agent to a high magnetic field (e.g. 1 T or more) at low temperature (e.g. 100 K or less);

(ii) exposing the agent to a $T_1$ shortening effect in order to attain thermodynamic equilibrium at said low temperature.

The $T_1$ shortening effect may be provided by exposure to a variable magnetic field gradient but it may also be achieved by adding magnetic material (e.g. paramagnetic, superparamagnetic or ferromagnetic materials) to the agent during the period when the agent is exposed to low temperature. A suitable $T_1$ shortening agent is Gd but preferred are $O_2$, NO or $NO^s$ which may be conveniently separated from the high $T_1$ agent before transportation and subsequent use.

In the fourth embodiment of the invention, both the high $T_1$ agent and the aqueous solvent (eg. water) in which it is dissolved may be polarised. This may be carried out at low temperature conveniently in the same magnetic field and after mixing the administrable composition should be warmed very rapidly prior to administration.

Thus viewed from a further aspect, the present invention provides an administrable composition comprising a polarised high $T_1$ agent and polarised water.

The high $T_1$ agents used in the method according to the invention may be conveniently formulated with conventional pharmaceutical or veterinary carriers or excipients. Formulations manufactured or used according to this invention may contain, besides the high $T_1$ agent, formulation aids such as are conventional for therapeutic and diagnostic compositions in human or veterinary medicine. Thus the formulation may for example include stabilizers, antioxidants, osmolality adjusting agents, solubilizing agents, emulsifiers, viscosity enhancers, buffers, etc. The formulation may be in forms suitable for parenteral (eg. intravenous or intraarterial) or enteral (eg. oral or rectal) application, for example for application directly into body cavities having external voidance ducts (such as the lungs, the gastrointestinal tract, the bladder and the uterus), or for injection or infusion into the cardiovascular system. However solutions, suspensions and dispersions in physiological tolerable carriers eg. water will generally be preferred.

For use in in vivo imaging, the formulation, which preferably will be substantially isotonic, may conveniently be administered at a concentration sufficient to yield a 1 micromolar to 10M concentration of the high $T_1$ agent (or even higher where the high $T_1$ agent is water) in the imaging zone; however the precise concentration and dosage will of course depend upon a range of factors such as toxicity, the organ targeting ability of the high $T_1$ agent and the administration route. The optimum concentration for the MR imaging agent represents a balance between various factors. In general, optimum concentrations would in most cases lie in the range 0.1 mM to 10M (or even higher where the high $T_1$ agent is water), preferably more than 10 mM, especially more than 100 mM. Isotonic solution may be especially preferred. In certain circumstances concentrations above 1M are preferred. Where water is the MR imaging agent the concentration is approximately 56M. Formulations for intravenous or intraarterial administration would preferably contain the high $T_1$ agent in concentrations of 10 mM to 10M (or even higher where the high $T_1$ agent is water), especially more than 50 mM. For bolus injection the concentration may conveniently be 0.1 mM to 56M, preferably more than 200 mM, more preferably more than 500 mM. In certain circumstances, the preferred concentration is above 1M, even more preferably above 5M. For water as the MR imaging agent the concentration is approximately 56M.

Parenterally administrable forms should of course be sterile and free from physiologically unacceptable agents, and should have low osmolality to minimize irritation or other adverse effects upon administration and thus the formulation should preferably be isotonic or slightly hypertonic. Suitable vehicles include aqueous vehicles customarily used for administering parenteral solutions such as Sodium Chloride solution, Ringer's solution, Dextrose solution, Dextrose and Sodium Chloride solution, Lactated Ringer's solution and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The compositions can contain preservatives, antimicrobial agents, buffers and antioxidants conventionally used for parenteral solutions, excipients and other additives which are compatible with the high $T_1$ agents and which will not interfere with the manufacture, storage or use of the products.

Where the high $T_1$ agent is to be injected, it may be convenient to inject simultaneously at a series of administration sites such that a greater proportion of the vascular tree may be visualized before the polarization is lost through relaxation.

The dosages of the high $T_1$ agent used according to the method of the present invention will vary according to the precise nature of the high $T_1$ agents used, of the tissue or organ of interest and of the measuring apparatus. Preferably the dosage should be kept as low as possible while still achieving a detectable contrast effect. In general, the maximum dosage will depend on toxicity constraints.

The invention is illustrated by the following Examples in a non-limiting manner:

EXAMPLE 1

A high $T_1$ agent is placed in a chamber at very low temperature (about 4 K). Fluent $O_2$ is added and crystallised on the surface of the high $T_1$ agent. In a separate chamber, frozen $H_2O$ is subjected to the same treatment as the high $T_1$ agent. Both chambers are placed in a strong magnetic field (about 15 T) and the temperature kept low.

When thermodynamic equilibrium is reached, the temperature is increased to about 200 K. The oxygen disappears as a gas. The high $T_1$ agent and the frozen $H_2O$ are mixed and stored until needed. The temperature is increased and the solution comprising polarised high $T_1$ agent and hyperpolarised water is injected.

EXAMPLE 2

300 mg of sterile $Na_2{}^{13}CO_3$ or $NaH^{13}CO_3$ is placed inside a 10 ml plastic injection syringe. The gas inside the syringe is enriched with >20% oxygen. The syringe is placed inside a magnet (1–20 T) at a temperature of about 4 K (0.001–5 K) until thermodynamic equilibrium is reached.

The syringe is removed and transported to the subject located in the MRI magnet. 10 ml of sterile Ringers Solution (at 37° C., pH 7.4) is aspirated and injected at a rate of 10 ml/sec immediately after the high $T_1$ agent has dissolved. $^{13}C$ MRI is performed using a fast pulse sequence. $T_1$ in the blood is about 20 s and the distribution of the agent is followed on the MR imager.

EXAMPLE 3

To a sample of sodium acetate (1-$^{13}C$) is added α, γ-bisphenyl-β-phenylallyl benzene complex (5% w/w). The compounds are milled together to give an intimate mixture, which is transferred to a borosilicate glass ampule. This is then repeatedly evacuated and filled with helium. The last time a pressure of a 200 mbar of helium is left in the ampule, which is then flame sealed.

The sample is polarized by microwaves (70 GHz) for at least one hour at a field of 2.5 T at a temperature of 4.2 K. The progress of the polarization process is followed by in situ NMR (fast adiabatic passage). When a suitable level of polarization has been reached, the ampule is rapidly removed from the polarizer and, while handled in a magnetic field of no less than 50 mT, cracked open and the contents are quickly discharged and dissolved in warm (40° C.) water.

Experiment 1: This solution is quickly transferred to a spectrometer and $^{13}C$ spectrum with enhanced intensity is recorded.

Experiment 2: The sample solution is inserted into an MRI machine with $^{13}C$ capability and a picture with enhanced intensity and contrast is obtained by a single shot technique.

Experiment 3: The solution is quickly injected into a rat and a $^{13}C$ MRI picture with enhanced intensity and contrast is obtained, also in this case, by utilization of a single shot technique.

EXAMPLE 4

To a sample of sodium bicarbonate —$^{13}C$ is added $MnCl_2$ (5% w/w). The compounds are milled together to give an intimate mixture, which is transferred to a borosilicate glass ampule. This is then repeatedly evacuated an filled with helium. The last time a pressure of a 200 mbar of helium is left in the ampule, which is then flame sealed.

The sample is polarized by microwaves (70 GHz) for at least 1 hour at a field of 2.5 T at a temperature of 4.2 K. The progress of the polarization process is followed by in situ NMR (fast adiabatic passage). When a suitable level of polarization has been reached, the ampule is rapidly removed from the polarizer and, while handled in a magnetic field of no less than 50 mT, cracked open and the contents are quickly discharged and dissolved in warm (40° C.) water.

Experiment 1: This solution is quickly transferred to a spectrometer and $^{13}$ C spectrum with enhanced intensity is recorded.

Experiment 2: The sample solution is inserted into an MRI machine with $^{13}C$ capability and a picture with enhanced intensity and contrast is obtained by a single shot technique.

Experiment 3: The solution is quickly injected into a rat and a $^{13}C$ MRI picture with enhanced intensity and contrast is obtained, also in this case, by utilization of a single shot technique.

What is claimed is:

1. A method of magnetic resonance investigation of a sample, said method comprising:

i) subjecting a high $T_1$ agent to ex vivo polarisation and where this is carried out by means of a polarising agent, optionally separating the whole, or a portion of said polarising agent from said high $T_1$ agent;

ii) administering said high $T_1$ agent to said sample;

iii) exposing said sample to a radiation of a frequency selected to excite nuclear spin transitions in selected nuclei;

iv) detecting magnetic resonance signals from said sample; and v) optionally, generating an image, dynamic flow date, diffusion data, perfusion data, physiological data or metabolic data from said detected signals, wherein said high $T_1$ agent is a solid high $T_1$ agent comprising nuclei selected from the group consisting of $^{1}H$, $^{3}L_{i}$, $^{13}C$, $^{15}N$, $^{19}F$ and $^{31}P$ nuclei and wherein said solid high $T_1$ agent is dissolved in an administrable media prior to administration to said sample.

2. A method as claimed in claim 1 wherein step i) comprises hyperpolarising a hyperpolarisable gas before, during or after introducing a high $T_1$ agent thereto whereby to cause nuclear polarisation of said high $T_1$ agent.

3. A method as claimed in claim 2 wherein said high $T_1$ agent has a $T_1$ value at a field strength of 0.01–5 T and a temperature in the range 20–40° C. of at least 2 secs.

4. A method as claimed in claim 2 wherein said high $T_1$ agent has a $T_1$ value at a field strength of 0.01–5 T and a temperature in the range 20–40° C. of at least 5 secs.

5. A method as claimed in claim 2 wherein said high $T_1$ agent has a $T_1$ value at a field strength of 0.01–5 T and a temperature in the range 20–40° C. of at least 10 secs.

6. A method as claimed in claim 2 wherein said high $T_1$ agent has a $T_1$ value at a field strength of 0.01–5 T and a temperature in the range 20–40° C. of at least 30 secs.

7. A method as claimed in claim 2 wherein said high $T_1$ agent has a $T_1$ value at a field strength of 0.01–5 T and a temperature in the range 20–40° C. of at least 70 secs.

8. A method as claimed in claim 2 wherein said high $T_1$ agent has a $T_1$ value at a field strength of 0.01–5 T and a temperature in the range 20–40° C. of at least 100 secs.

9. A method as claimed in claim 2 wherein said high $T_1$ agent contains $^{13}C$ nuclei.

10. A method as claimed in claim 9 wherein said high $T_1$ agent has $^{13}C$ at one particular position in its molecular structure in an amount above 1%.

11. A method as claimed in claim 9 wherein said high $T_1$ agent has $^{13}C$ at one particular position in its molecular structure in an amount above 5%.

12. A method as claimed in claim 9 wherein said high $T_1$ agent has $^{13}C$ at one particular position in its molecular structure in an amount above 10%.

13. A method as claimed in claim 9 wherein said high $T_1$ agent has $^{13}C$ at one particular position in its molecular structure in an amount above 25%.

14. A method as claimed in claim 9 wherein said high $T_1$ agent has $^{13}C$ at one particular position in its molecular structure in an amount above 50%.

15. A method as claimed in claim 9 wherein said high $T_1$ agent has $^{13}C$ at one particular position in its molecular structure in an amount above 99%.

16. A method as claimed in claim 9 wherein said high $T_1$ agent is $^{13}C$ enriched at one or more carbonyl or quaternary carbon positions.

17. A method as claimed in claim 16 wherein said high $T_1$ agent is deuterium labelled.

18. A method as claimed in claim 17 wherein said deuterium label is adjacent a $^{13}C$ nucleus.

19. A method as claimed in claim 2 wherein said high $T_1$ agent contains $^{19}F$ nuclei.

20. A method as claimed in claim 2 wherein said high $T_1$ agent exhibits at 1 T a chemical shift of more than 2 ppm.

21. A method as claimed in claim 2 wherein said high $T_1$ agent exhibits at 1 T a chemical shift of more than 10 ppm.

22. A method as claimed in claim 2 wherein said hyperpolarisable gas is a noble gas.

23. A method as claimed in claim 22 wherein said noble gas is selected from the group consisting of He and Xe.

24. A method as claimed in claim 22 wherein said noble gas is $^3He$.

25. A method as claimed in claim 2 wherein said hyperpolarisable gas is an alkali metal vapour.

26. A method as claimed in claim 25 wherein said alkali metal vapour is selected from the group consisting of Na, K, Rb and Cs vapours.

27. A method as claimed in claim 2 wherein said hyperpolarisable gas is used in liquid or solid form.

28. A method as claimed in claim 2 wherein said hyperpolarisable gas is a mixture of two or more gases.

29. A method as claimed in claim 2 wherein said hyperpolarisable gas has a hyperpolarisation half-life of at least 1000 secs.

30. A method as claimed in claim 2 wherein said hyperpolarisable gas has a hyperpolarisation half-life of at least 4000 secs.

31. A method as claimed in claim 2 wherein said hyperpolarisable gas has a hyperpolarisation half-life of at least 8000 secs.

* * * * *